(12) United States Patent
Cumming et al.

(10) Patent No.: US 8,262,601 B2
(45) Date of Patent: Sep. 11, 2012

(54) HELMET TRAUMA BANDAGE AND METHOD

(76) Inventors: Michelle Cumming, Pacific Grove, CA (US); Mitchell Kastros, Carmel, CA (US)

(*) Notice: Subject to any disclaimer, the term of this patent is extended or adjusted under 35 U.S.C. 154(b) by 192 days.

(21) Appl. No.: 12/807,288

(22) Filed: Sep. 1, 2010

(65) Prior Publication Data

US 2010/0331752 A1 Dec. 30, 2010

Related U.S. Application Data

(63) Continuation-in-part of application No. 12/586,431, filed on Sep. 22, 2009, now abandoned, which is a continuation-in-part of application No. 12/156,512, filed on Jun. 2, 2008, now abandoned.

(51) Int. Cl.
| | |
|---|---|
| A61F 13/12 | (2006.01) |
| A61F 5/00 | (2006.01) |
| A61F 13/00 | (2006.01) |
| A61F 15/00 | (2006.01) |
| A61F 7/00 | (2006.01) |
| A42B 1/04 | (2006.01) |

(52) U.S. Cl. ............... 602/74; 602/60; 602/41; 602/42; 602/14; 602/2; 607/114; 607/109; 607/110; 607/112; 2/171; 2/171.2; 2/417

(58) Field of Classification Search ............ 602/74, 602/60, 53, 61, 2, 14, 41, 42, 79; 607/114, 607/109, 110, 108, 112; 128/857, 888, 846; 2/410, 171.2, 171, 417; 606/20
See application file for complete search history.

(56) References Cited

U.S. PATENT DOCUMENTS

| | | |
|---|---|---|
| 945,839 A | 1/1910 | Brisbane |
| D295,446 S | 4/1988 | Lundell et al. |
| 4,744,106 A | 5/1988 | Wang |
| 5,031,609 A | 7/1991 | Fye |
| 5,044,031 A | 9/1991 | Sherwood |
| 5,173,970 A | 12/1992 | Shifrin |
| 5,305,470 A | 4/1994 | McKay |
| D354,376 S | 1/1995 | Kun |
| 5,557,807 A | 9/1996 | Hujar et al. |
| 5,666,668 A | 9/1997 | Ronquillo |
| 5,860,292 A | 1/1999 | Augustine et al. |
| 5,960,477 A | 10/1999 | Dixon |
| 6,228,041 B1 | 5/2001 | Ameer |
| 6,678,896 B2 | 1/2004 | Robinson et al. |
| 6,747,561 B1 | 6/2004 | Reeves |
| 6,762,337 B2 | 7/2004 | Boukanov et al. |
| 2005/0027227 A1 | 2/2005 | Dumas et al. |
| 2005/0193491 A1 | 9/2005 | Zucker et al. |
| 2007/0074326 A1 | 4/2007 | Komechak |

*Primary Examiner* — Patricia Bianco
*Assistant Examiner* — Victoria J Hicks
(74) *Attorney, Agent, or Firm* — Marcus G. Theodore

(57) ABSTRACT

An emergency helmet trauma bandage and method of use, which, when applied, applies minimal pressure to stop bleeding, doesn't compromise cervical spine immobilization, allows for fast and effective application of ice/cold packs to control intracranial/internal swelling, doesn't come apart during treatment and transport, and doesn't require a caregiver to re-wrap the dressing.

9 Claims, 4 Drawing Sheets

HELMET TRAUMA BANDAGE AND METHOD

RELATED APPLICATIONS

This application is a continuation-in-part patent application of the continuation-in-part patent application entitled "Head Trauma Bandage and Method", Ser. No. 12/586,431, filed Sep. 22, 2009, now abandoned which is a continuation-in-part of the patent application entitled "Head Trauma Cap Bandage", Ser. No. 12/156,512 filed Jun. 2, 2008 now abandoned.

BACKGROUND OF THE INVENTION

1. Field

The present invention relates to bandages and trauma treatment. In particular, it relates to a method of use and an emergency helmet trauma bandage with pouches for hot or cold packs, which is placed on the cranium to cover the crown, forehead, back of the head, the temples and ears of an injured patient with minimal movement of the neck and spine.

2. Description of Related Art

Various bandages are known in the art. Boukanov et al., U.S. Pat. No. 6,762,337 issued Jul. 13, 2004 discloses a multi-purpose pressure bandage for body wounds utilizing an expansion bladder, which inflates to compress an affixed bandage against an injured patient's wounds. The Boukanov et al. specifically states its system design is to provide a pressure dressing. To apply pressure, the device incorporates the use of a carbon dioxide gas container with an inlet valve for inflating a bladder in the bandage on site to apply additional pressure (resistance pressure or inflating to create pressure) to the wound to control bleeding.

The Boukanov et al. embodiment for head wounds has the compression bandage shaped like a cap to secure about the head. The Boukanov et al head bandage configuration has a bladder with a coextensive gauze bandage liner and a gas cartridge hidden in a pouch at a bottom edge. Elongated hook and loop straps extend diametrically from the bottom edge for securing the dome-shaped pressure bandage to a head injury. Once in place, the bandage is inflated to apply pressure to the wound. Although the application of pressure to control bleeding is taught to be the standard when treating soft tissue injuries, it is contraindicated with regard to bleeding associated with a head injury.

Boukanov et al.'s compression bandage is not suitable for head injuries. Head injuries are usually associated with intracranial swelling which causes excess pressure on the brain and towards the skull. Pressure treatment similar to Boukanov et al. applied to a head injury through compression compounds the problem of internal pressure to the brain and skull. Through this compression method the pressure applied by treating the injury creates even more pressure on the brain, and this can lead to a rapid deterioration of the condition of the patient. In addition, long-term and permanent brain damage can occur from the application of a pressure dressing, which, in the worst case, can lead to the death of the patient.

The standard of treatment for a head injury is to apply gentle pressure for controlling bleeding, and for applying ice to control intracranial swelling associated with head trauma. The idea of applying "gentle pressure" is to not exceed the amount of pressure being exerted inside the cranium resulting from head trauma.

The present invention discussed below is designed to be consistent with the standard for treating head injuries, and does not have any similarities with the Boukanov et al compression system with regard to its application. It does not have any features which create excess pressure, compromise cervical-spinal precautions or in any other way challenge the well-being of the patient with a head injury.

If the Boukanov et al. pressure regulation fails, it also may result in significant pressure, which can cause serious head injuries where intra cranial fluids build up causing the head to swell. In addition, if improperly inflated, circulation may be cut off. The bandage also suffers from compression problems if the gas container is empty, or fails to inflate the bladder. Under these circumstances, the Boukanov et al pressure bandage may aggravate the patient's head injuries. Further, if the Boukanov et al. bladder is pierced accidentally during emergency use, an ill fitting head wrap results.

Lundell et al., U.S. Design Patent, Des. 295,446, issued Apr. 26, 1988 is a head bandage protector that would require first conventionally wrapping the patent with bandages, which may compromise cervical spin immobilization depending on how the bandage wraps are administered.

Fye, U.S. Pat. No. 5,031,609, issued Jul. 16, 1991 is a postoperative compression bandage for the head, which would also require conventional bandaging before compression application; again possibly compromising cervical spine immobilization.

Neither Lundell et al, nor Fye are bandages with a weather resistant cover for rapid application in the field to avoid moving the neck or spine during emergency trauma applications.

Cited for general interest are: Sherwood, U.S. Pat. No. 5,044,031, issued Sep. 3, 1991 discloses passive warming articles for traumatized individuals suffering from hypothermia, shock or exposure. Kun, U.S. Pat. No. Des. 354,376, issued Feb. 14, 1995 discloses a head cooling cap. Hujar et al., U.S. Pat. No. 5,557,807 issued Sep. 24, 1996 discloses headwear including coolant means. Ameer, U.S. Pat. No. 6,228,041, issued May 8, 2001 discloses a lightweight portable scalp vibrating and hair growth stimulating device. Komachak U.S. Publication No. US2007/0074326, dated Apr. 5, 2007, discloses a headgear with cooling device formed using a woven or non-woven material. Wang, U.S. Pat. No. 4,744,106, issued May 17, 1988 discloses an engineering cap with fan device structure for ventilation of the hard hat. Augustine et al., U.S. Pat. No. 5,860,292 issued Jan. 19, 1999 discloses an inflatable thermal blanket with head covering for convectively cooling the body. Robinson et al., U.S. Pat. No. 6,678,896, issued Jan. 20, 2004 discloses a sports towel. Ronquillo, U.S. Pat. No. 5,666,668 issued Sep. 16, 1997 discloses a cap with front size adjustment and rear flap. Dixon, U.S. Pat. No. 5,960, 477 issued Oct. 5, 1999 discloses a hat with folded rim and visor. Dumas et al., U.S. Pub. No. 2005/0027227 published Feb. 3, 2005 discloses a disposable water resistant cover for medical applications. Reeves, U.S. Pat. No. 6,747,561 issued Jun. 8, 2004 discloses a bodily worn device, which provides for digital storage and retrieval of a user's medical records, drug prescriptions, medical history, organ donor instructions, and personal identification for use in an emergency or routine medical situation. Zucker et al., U.S. Publication No. US2005/0193491 published Sep. 8, 2005, discloses a pediatric emergency transport device. McKay, U.S. Pat. No. 5,305,470, issued Apr. 26, 1994 discloses a sports band. Brisbane, U.S. Pat. No. 945,839, issued Jan. 11, 1910 is not a sleeping cap unsuitable for use as a bandage, and may not expand sufficiently to accommodate larger heads. The elasticized Brisbane sleeping cap using elasticized side to apply pressure for holding the cap onto the head could adversely affect intracranial pressure from a head wound and aggravate the wound tissue when slid over the head. Dixon, U.S. Pat. No. 5,960,477, issued Oct. 5, 1999, is a snow hat with folded rim requiring the head to be lifted for placement, again aggravating spinal injuries. Dumas et al. U.S. Publication 2005/0027227 published Dec. 3, 2005 is a medical disposable water resistant cover for medical applications. Shifrin, U.S. Pat. No. 5,173,970, issued Dec. 29, 1992 discloses a visored cap-type protective segmented helmet for bicyclists and the like, which can be used as a pouch.

None of the above references provides an emergency head bandage, which doesn't compromise cervical spine immobilization, when applied, doesn't come apart during treatment and transport, and doesn't require a caregiver to re-wrap the dressing. The improved invention discussed below can be quickly applied as a bandage dressing to control bleeding and/or a device to secure ice packs to gently control intracranial pressure. These features can be used separately or in conjunction with a single application of the cap, depending on the medical needs of the patient with regard to head trauma. The invention described below provides such an invention and method of using it.

SUMMARY OF THE INVENTION

The present invention comprises a helmet trauma bandage. It is structured as a flexible stretchable helmet with periphery edges, segments, and an opening sized to fit about and cover the forehead/crown, sides/ears, and back of the head of a patient with a head trauma. The helmet segments proximate the ears defining ear opening observation holes to reveal any fluid discharge through the ears.

A sterile dressing liner is affixed to the inside of the helmet. The helmet and liner are made of a material with enough stretch when placed on a patient to apply minimal pressure to the head to control bleeding without aggravating intracranial pressure.

Exterior pouches are affixed to the exterior of the stretchable cap and structured to removably receive and secure therein hot or cold packs. The type of cold pack is selected depending upon whether cold applications are required to stop further swelling, or whether hot applications are required to help prevent hypothermia in non-head trauma situations.

A strap system is releaseably affixed to the helmet periphery edges and structured to pass under a patient's chin to secure the helmet with openable, adjustable, fastening ends in a manner to apply minimal pressure to control bleeding and loosened and re-attached to prevent circulation stoppage and avoid aggravating intracranial pressure.

In one embodiment, there are four exterior pouches positioned to cover respectively the forehead/crown, back and sides/ears of the head. Each pouch is structured with top openings leading into interiors into which hot or cold packs are inserted and secured therein with openable fasteners before subsequent removal.

In one embodiment, the periphery segments of the helmet defining the ear observation holes are slit and variably secured together with adjustable ear straps to vary the size of their openings so that the helmet better fits about the ear segments. One embodiment has one end of the ear straps secured to the helmet on the one side of the slit. An openable and closable adjustment fastener is affixed to a second end of the ear strap extending to the other side of the slit. The adjustment fastener structured to secure to corresponding fastener affixed to the helmet proximate the other side of the slit in a manner so that the opening of the observation holes may be varied in size as the strap fastener is varied in position.

Preferred fasteners are hook and loop strips. Other fasteners, such as snaps, hooks, buttons, etc. could be used to secure the strap ends, but these are more complicated to use in the field, and are more expensive and difficult to adjust.

Preferred construction is with ultrasonic seaming and welding as it does not use needles and thread, eliminating color change and thread unraveling. Seam welding is particularly suited to secure inner gauze liners to the shell to prevent frayed ends. These ultrasonic sewing machines are also suited for use in clean room production facilities. However, where cotton fabrics are used employed, conventional sewing may be required.

In one embodiment, the helmet is constructed of a stretchable weather resistant material. The helmet may be color coded and placed on the patient to indicate the severity of a patient's injuries. Color codes are also used to identify patients who have been given a medication or treatment, which requires special handling by emergency trauma teams. This is particularly important for field disasters requiring triage color categorization. In advanced triage systems, secondary triage is typically implemented by paramedics, battlefield medical personnel or by skilled nurses in the emergency departments of hospitals, and during disasters, where injured people are sorted into five categories (note; categories and color coordinates may vary according to regions and other requirements dictated by policy:

Black/Expectant (Monterey County, California category is "Morgue," Pulseless/Non-Breathing)

They are so severely injured that they will die of their injuries, possibly in hours or days (large-body burns, severe trauma, lethal radiation dose), or in life-threatening medical crisis that they are unlikely to survive given the care available (cardiac arrest, septic shock, severe head or chest wounds); they should be taken to a holding area and given painkillers as required to reduce suffering.

Red/Immediate (same in Monterey County, California)

They require immediate surgery or other life-saving intervention, and have first priority for surgical teams or transport to advanced facilities; they "cannot wait" but are likely to survive with immediate treatment.

Yellow/Observation (Monterey, California category is "Delayed," Serious, Non-Life Threatening)

Their condition is stable for the moment but requires watching by trained persons and frequent re-triage, will need hospital care (and would receive immediate priority care under "normal" circumstances).

Green/Wait (walking wounded) (Monterey County, California category is "Minor")

They will require a doctor's care in several hours or days but not immediately, may wait for a number of hours or be told to go home and come back the next day (broken bones without compound fractures, many soft tissue injuries).

White/Dismiss (walking wounded)

They have minor injuries; first aid and home care are sufficient, a doctor's care is not required. Injuries are along the lines of cuts and scrapes, or minor burns.

By color coding the bandage wraps by attaching triage tags to them or actually employing different colored caps, traumatized patients can quickly be directed for appropriate care.

The helmet trauma bandage for covering a head wound of a patient is used by affixing over a traumatized patient's head, a flexible stretchable helmet with i. periphery edges, segments, and an opening sized to fit about and cover the forehead, crown, ears, and back of the head of a patient with a head trauma; the helmet segments covering the ears defining ear opening observation holes to reveal any bleeding or excretion of cerebrospinal fluid through the ears, and the helmet edges, ii. a sterile dressing liner affixed to the inside of the helmet; said helmet and liner with enough stretch when placed on a patient to apply minimal pressure to the head to control bleeding without aggravating intracranial pressure, iii. exterior pouches affixed to the exterior of the stretchable cap structured to removably receive and secure therein hot or cold packs, and iv. a strap system releaseably affixed to the helmet periphery edges and structured to pass under a patient's chin to secure the helmet with openable, adjustable, fastening ends about the head in a manner to apply minimal pressure to control bleeding and loosened and re-attached to prevent circulation stoppage and avoid aggravating intracranial pressure.

The strap system is then secured to hold the helmet bandage against the patient's head to apply minimal pressure to stop bleeding.

Where head or spinal injuries are present or suspected, the patient is immobilized first before applying the helmet trauma bandage. In addition, different colored helmet trauma bandages to indicate different triage categories may be applied to indicate the severity of a patient's injuries, and are selectively applied to a patient to indicate the type of medical response required.

The method of using a helmet trauma bandage exterior pouches also may vary to accommodate removable ice packs or hot packs, which are selectively employed when needed to reduce swelling when ice packs are applied, or preserve body heat in non-head trauma situations when heat packs are applied.

The stretchable helmet trauma bandage allows the head to swell from cranial pressure, but provides sufficient contact with the wound to minimize bleeding. It is particularly suited for emergency field use, where rapid stabilization of a patient is required for transport. Minor cuts on the head often bleed heavily because the face and scalp have many blood vessels close to the surface of the skin. This bleeding is alarming, but often the injury is not severe and the bleeding will stop with modest pressure treatment. Head wounds encountered in the field, must be quickly covered to minimize bleeding to stabilize the patient for rapid transport for emergency treatment. Traditional bandaging requires multiple strips of gauze or sterile wrappings to be wound about the patient's head. This is often time consuming and often requires the head to be repeatedly lifted or moved, which can aggravate spinal injuries.

The Boukanov type flexible cap bandage may aggravate open wounds by acting as a compression bandage applying too much cranial pressure, The present flexible helmet trauma bandage is quickly applied over the cranium in a manner, which does not compromise cervical spine immobilization, which can occur with conventional bandage wrapping. It not only stops bleeding, but it does not overly apply excessive pressure on the wound to stop circulation or aggravate intracranial pressure.

If head swelling occurs, the flexible helmet trauma bandage's securing straps may be loosened and re-affixed to prevent increasing intracranial pressure.

On the inside of the helmet trauma bandage is attached a stretchable sterile dressing liner. The stretchable helmet and dressing liner has enough stretch when placed on a patient to allow expansion and apply minimal pressure to control bleeding and hold the cap bandage in place.

It also has sufficient size, when secured, to accommodate swelling and hold the icepacks/cold packs placed in pouches in place about the patent's head for closed dermal head injuries (hematomas) to control swelling. These external pouches are attached around the helmet exterior into which the ice packs may be inserted to avoid contaminating the dressing liner or producing an ill fitting wrap bandage.

The wrap and sterile dressing liner are both preferably constructed of absorbent cotton, which stretches approximately 20% to apply minimal resistance pressure to stop bleeding. It also has sufficient give to accommodate wound swelling. The helmet trauma bandage with sterile dressing liner is packaged in a sterile wrap, which is removed just prior to use. It is inexpensive to manufacture, and may include a flexible liquid impervious helmet cover, for outdoor use to provide weather protection as the typical material used, cotton lycra, does bead up and does not soak through right away, but eventually soaks into the fabric and sterile liner.

As the trauma bandage wrap is a one-piece dressing and bandage, it is designed for simple, safe and quick application to the patient's head to control bleeding while minimizing movement to the patient's head. The biggest challenge in treating a head injury with bleeding is to minimize movement of the patient's head while effectively applying a dressing which will treat the wound and remain secure and intact on the patient's head. In any situation involving a head injury, with or without bleeding, there is also the chance of injury to the neck, back and spinal column. While treating the patient it is extremely important to minimize any action which will cause the head to move, possibly resulting in further injury to the spinal region. Protocols for the treatment of head injuries dictate caregivers to apply a cervical collar around the patient's neck and then secure the patient to a backboard in order to protect the spine. In the emergency medical field the helmet trauma bandage will be slid on and secured to the patient's head by one caregiver while a second caregiver maintains cervical spinal immobilization on the patient's head according to protocol, either before or after the patient is placed on the backboard. The proper application of the helmet trauma bandage minimizes head and neck movement, which reduces the chances of cervical-spinal compromise to the patient.

With traditional methods of treating head trauma, a separate dressing is applied to the wound followed by a wrap bandage which is wound in such a way as to secure the dressing to the wound. This method has its drawbacks as, based on the location of the wound on the head plus other challenges such as hair thickness, possible head movement etc., it is often difficult to secure the bandage. This results in the bandage slipping off of the patient's head and the need to re-apply a new dressing. In situations involving major head trauma, this can be critical in terms of blood loss, head movement, spinal column compromise and extended on-scene time.

The helmet trauma bandage is capable of being applied in such a way to quickly, safely and effectively cover and secure whichever part of the head needs protecting. When placed in position, it covers the top/forehead, sides/ears, and back of the head, which are the areas which cause challenges using traditional bandaging methods.

The invention is thus particularly suited for emergency treatment of accident victims with head wounds. These are quickly bandaged before patient transport, thereby reducing triage time. This allows the patient to be more rapidly transported to a hospital where the helmet bandage is quickly removed for examination and the wound treated.

The helmet trauma bandage is thus readily slid onto the head of a traumatized patient in the field. It is particularly suited to be placed in a manner to not interfere with cervical spine immobilization of an immobilized patient with spinal or neck injuries. As the invention is of one piece construction, it will not come apart during treatment or transport. It is fast and easy to apply to not only apply gentle direct pressure to a head wound, but also to control the bleeding to enable other treatment of the patient to be completed. If bleeding is profuse and if needed, additional dressings may be inserted beneath the bandage wrap to absorb and control bleeding.

The invention thus provides an emergency head bandage, which doesn't compromise cervical spine immobilization, when applied, doesn't come apart during treatment and transport, and doesn't require a caregiver to re-wrap the dressing.

DESCRIPTION OF THE ILLUSTRATED EMBODIMENTS

Figure 1:
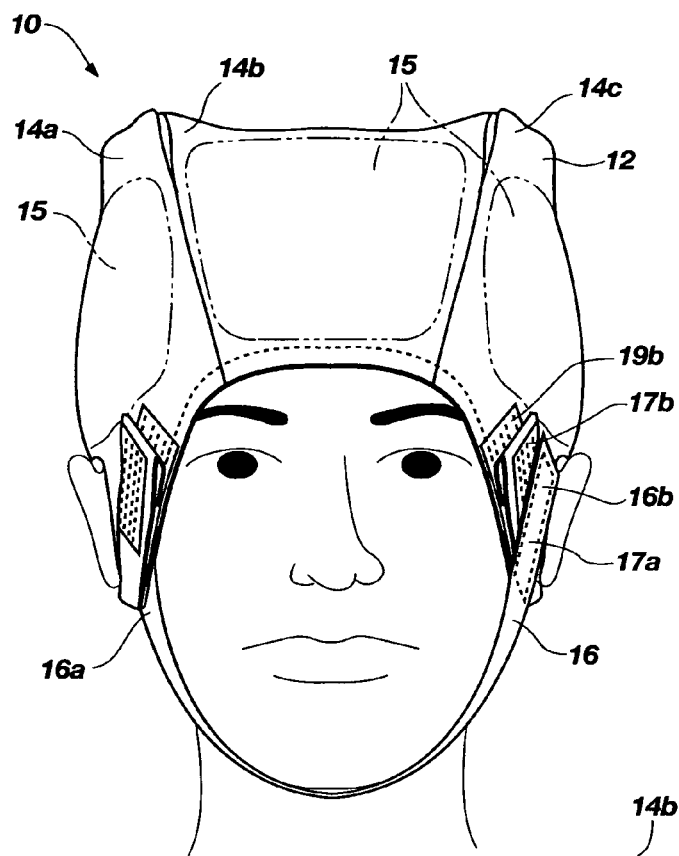
FIG. 1 is a front view of a preferred embodiment of the invention.

FIG. 1 illustrates a front view of a preferred embodiment of the invention 10, shown affixed about the head of a patient. It comprises a stretchable flexible helmet 12 with enough stretch to fit about the forehead, back, sides, and upper part of a patient's head securing the helmet 12 with ear holes 13a, 13b shown in FIGS. 3, 4 about the ears of a patient. The stretchable flexible helmet 12 applies gentile compression force around the head to stop bleeding, but is structured to be loosened and re-attached to prevent circulation stoppage and avoid aggravating intracranial pressure.

Figure 2:
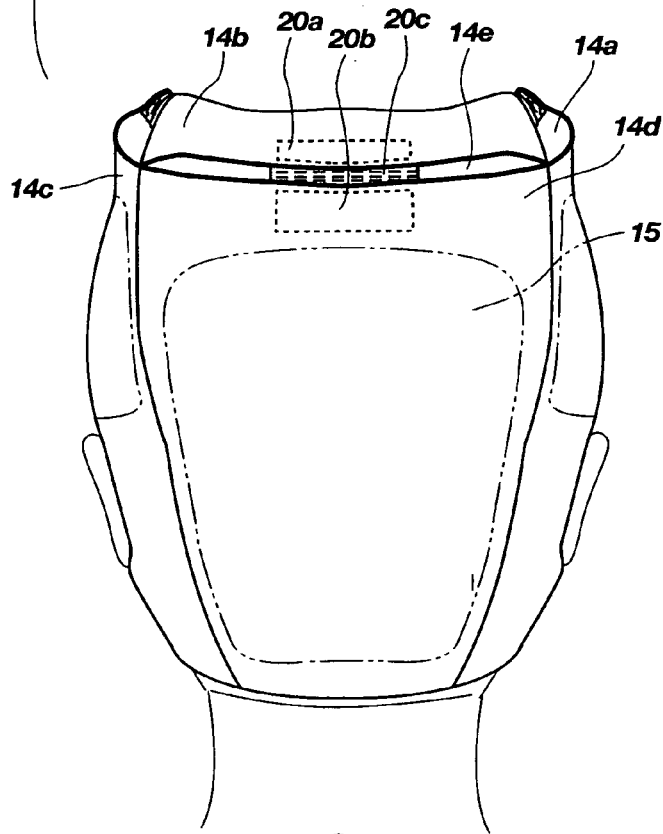
FIG. 2 is a rear view of the embodiment shown in FIG. 1.

FIG. 1 also shows ice pouches 14a, 14b and 14c which are designed to hold insertable ice packs 15 on the exterior of the flexible helmet 12 proximate the forehead and sides of the head to control intracranial swelling as the result of a head injury. FIG. 2 shows ice pouch 14d positioned on the exterior of the flexible helmet 12 proximate the back of the head to similarly control intracranial swelling.

To secure the helmet 12 in place, adjustable strap 16 with one end 16a affixed to the bottom of one of the peripheral edges of the sides of the helmet 12. The other end 16b of the adjustable strap 16 has a hook and loop strip 17a which secures to a corresponding hook and loop strip 17b to hold the helmet 12 in place about the head. The adjustable strap 16 allows additional gentle pressure to be applied by adjusting the hook and loop strips 17a, 17b to hold the helmet 12 anchored from under the chin about the head to control bleeding.

Figure 3:
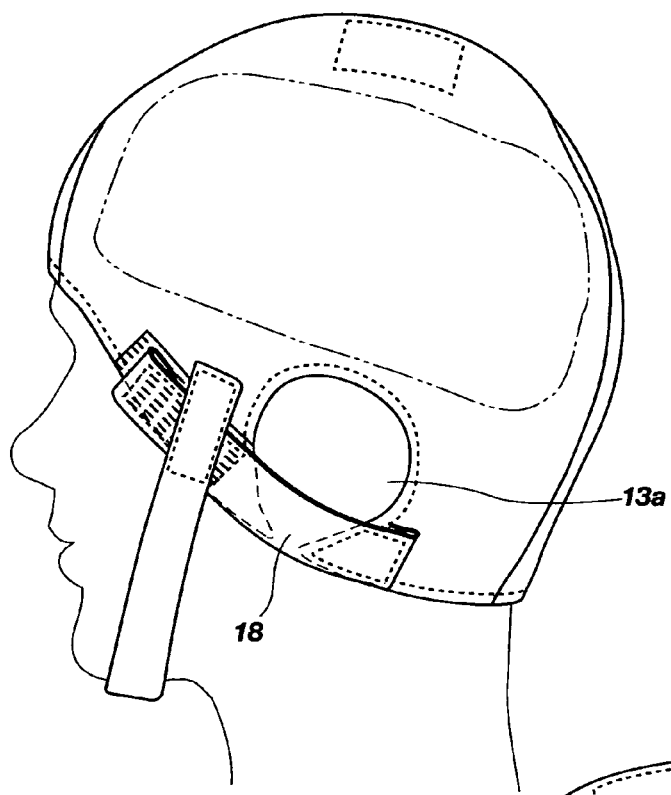
FIG. 3 is a side view of the embodiment shown in FIG. 1.
Figure 4:
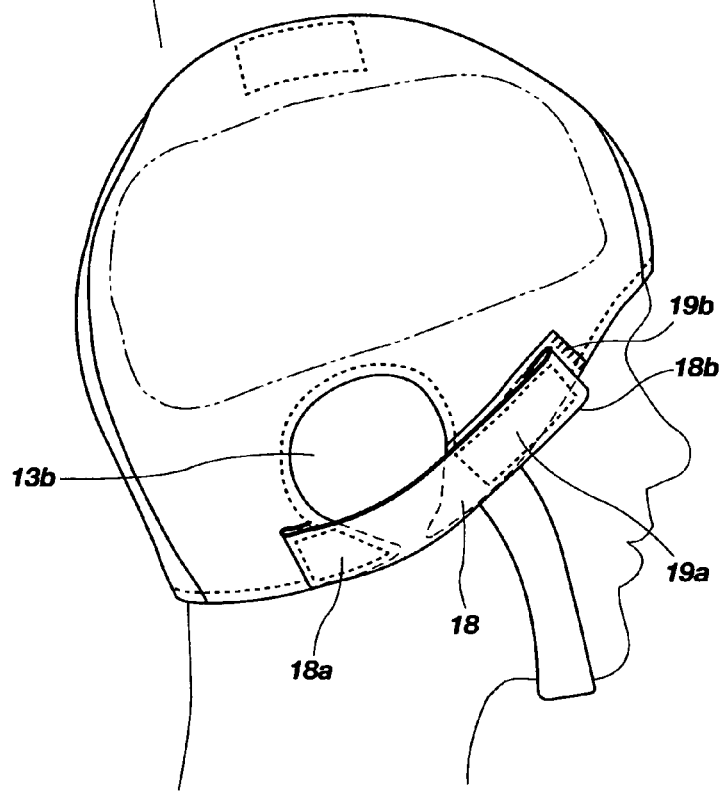
FIG. 4 is the other side view of the embodiment shown in FIG. 1.

Further adjustments are made with adjustable straps 18 shown in FIGS. 3 and 4 which adjust the opening of the ear holes 13a, 13b. One end 18a of adjustable straps 18 is affixed to the peripheral edge of the helmet 12 and the other end 18b has hook and loop strips 19a adapted to attach to corresponding hook and look strip 19b to also adjust and help fit and secure helmet 12 about the ears. In one embodiment, adjustable strap 18 is permanently attached to hook and loop strip attachment 19a and is secured to hook and loop strip 19b after looping under the patient's chin as FIG. 1 illustrates.

FIG. 2 is a rear view of the embodiment shown in FIG. 1. FIG. 2 shows ice pouch 14d, which is designed to hold an ice pack 15 on the rear of flexible helmet 12 (when secured to the patient's head). This pouch 14d is filed to control intracranial swelling as the result of a head injury along with filling pouches 14a, 14b, 14c for the front, sides and rear of the helmet 12 as shown in FIGS. 1 and 2.

Ice pouches 14a, 14b, 14c, and 14d have an opening 14e shown in FIG. 2 leading into an interior structured to removably hold ice packs 15 therein. Hook and loop strips 20a and 20b are attached to ice pouches 14a, 14b, 14c, and 14d, which in turn attach to hook and loop strips 20c in order to secure ice packs 15, which are inserted into ice pouches 14a, 14b, 14c, and 14d as shown in FIG. 2.

Figure 6:
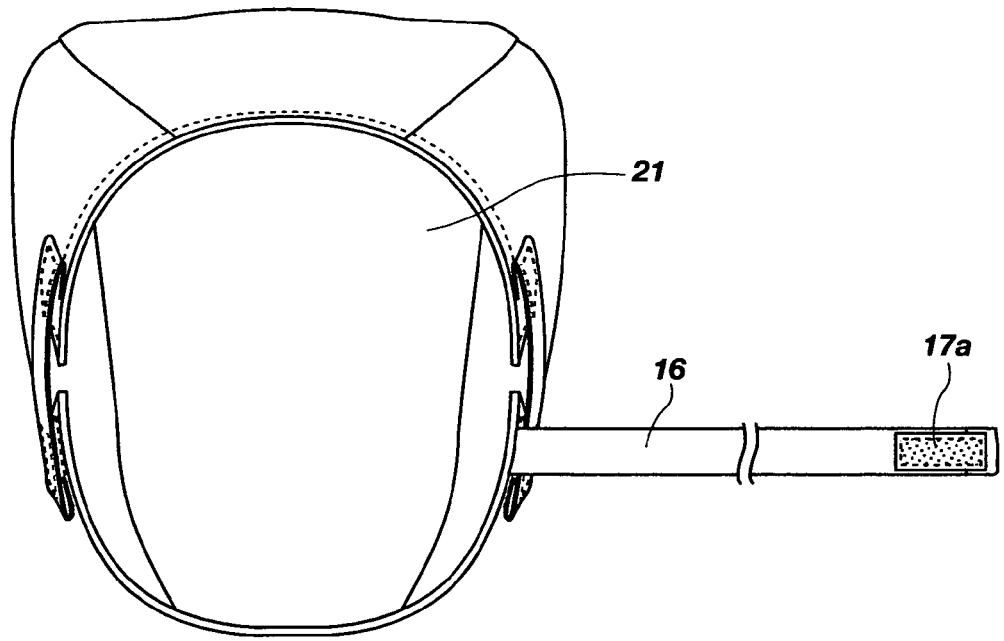
FIG. 6 is an interior view of the embodiment shown in FIG. 1.

On the inside of the helmet 12 is attached a sterile dressing liner 21 shown in FIG. 6. The stretchable helmet 12 and liner 21 have enough stretch when placed on a patient to apply gentle pressure to control bleeding. It is also stretchable to hold icepacks 15 in place, where necessary, about the patent's head for a closed dermal head injury (hematomas).

The helmet 12 and sterile dressing liner 21 are preferably constructed of absorbent cotton, which stretches approximately 20% to apply gentle pressure on a head wound. It also has sufficient give to accommodate wound swelling.

Figure 7:
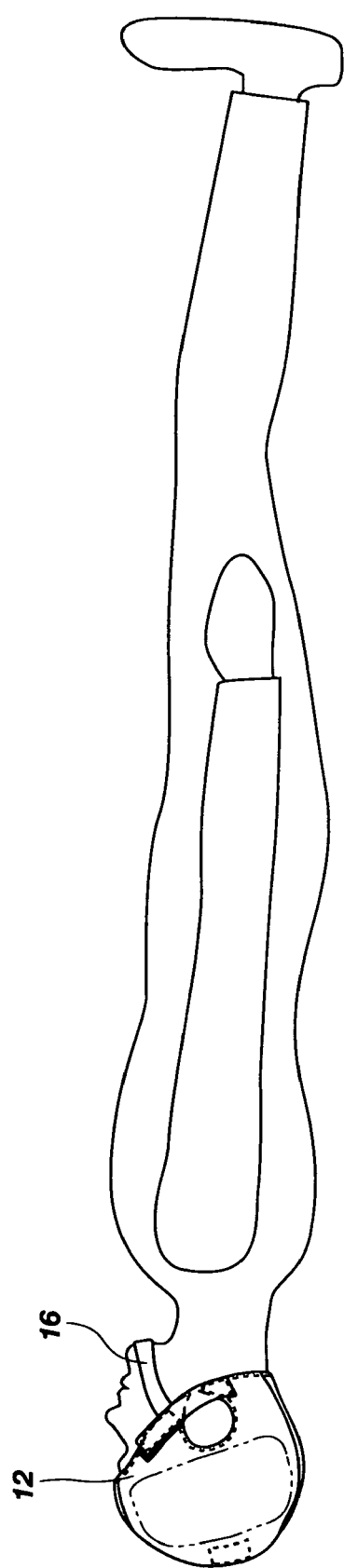
FIG. 7 is a perspective view of the embodiment of the invention shown in FIG. 1 applied to an immobilized patient.

The invention 10 is readily slid onto the head of a traumatized patient in the field while maintaining cervical spine immobilization as shown in FIG. 7. As the invention 10 is of one piece construction, it will not come apart during treatment or transport. It is fast and easy to apply to not only apply gentle pressure to the head wound, but also to control the bleeding to enable other treatment of the patient to be completed. If bleeding is profuse and if needed, additional dressings may be inserted beneath the helmet to control bleeding.

FIG. 3 shows a side view of helmet bandage 12 depicting the left side of the helmet 12 affixed to the patient's head. The adjustable strap 16 has a corresponding hook and loop strip 16b, which secure to a corresponding hook and loop strip 18a of strap 18 affixed to the corresponding strip 19b affixed to the helmet 12 to hold the helmet 12 in place about the head. The adjustable strap 16 allows additional gentle pressure to be applied by tightening both straps 16, 18 to corresponding hook and loop strips 16b, 18a, 19b to hold the helmet 12 anchored from under the chin about the head to control bleeding and help fit and secure cap 12 about the ears.

FIG. 3 shows ice pouch 14c which is designed to hold an ice pack 15 on the left side of flexible helmet 12 (when secured to the patient's head) and control intracranial swelling as the result of a head injury. Hook and loop strips 20a attach to ice pouch 14c as previously discussed in order to secure inserted ice packs 15.

Ear hole 13a exposes the left ear of the patient to allow emergency responders to monitor the absence or presence of cerebrospinal fluid and or blood which may result from head trauma to the patient.

FIG. 4 shows ice pouch 14b which is designed to hold an ice pack 15 on the right side of the flexible helmet 12, and similarly secures ice packs 15 therein. Ear hole 13b similarly allowed monitoring of the absence or presence of fluids resulting from head trauma.

Figure 5:
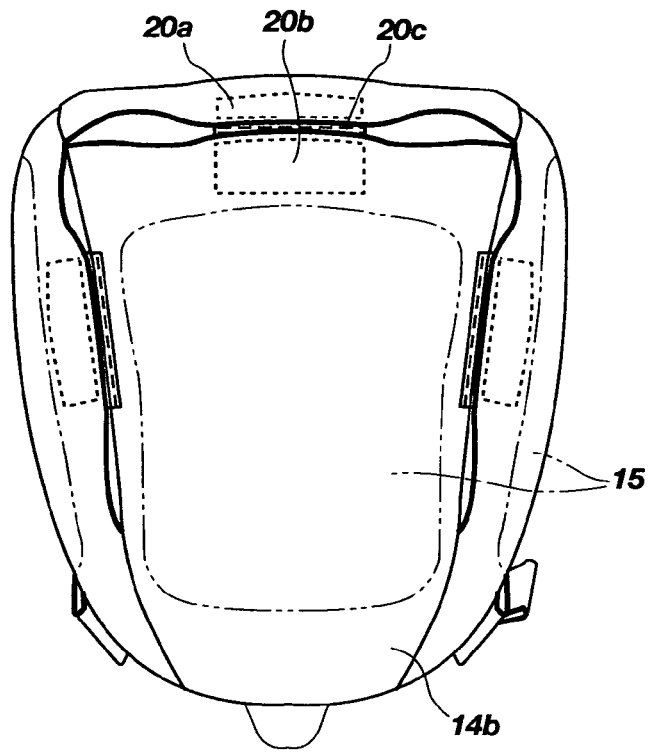
FIG. 5 is a top view of the embodiment shown in FIG. 1.

FIG. 5 shows a top view of the helmet 12 when placed on the head of the patient. The pouch 14a accommodates an ice pack 15, which covers the forehead and top of the head to reduce swelling.

FIG. 7 depicts a side view of the patient in the position he or she would be in when secured to a backboard wearing helmet 12 secured to the patient's head with adjustable strap 16.

The above description and specification should not be construed as limiting the scope of the claims but as merely providing illustrations of some of the presently preferred embodiments of this invention. Thus, the claims themselves contain those features deemed essential to the invention.

We claim:

1. A helmet trauma bandage comprising:
   a. a flexible stretchable helmet with periphery edges, segments, and an opening sized to fit about and cover a forehead/crown, sides/ears, and back of a head of a patient with a head trauma; the helmet segments configured to be positioned proximate the ears defining ear opening observation holes to reveal any fluid discharge through the ears,
   b. a sterile dressing liner affixed to the inside of the helmet; said helmet and liner with enough stretch when placed on the patient to apply minimal pressure to the head to control bleeding without aggravating intracranial pressure,
   c. exterior pouches affixed to the exterior of the stretchable helmet structured to removably receive and secure therein hot or cold packs, and
   d. a strap system releaseably affixed to the helmet periphery edges and structured to pass under a patient's chin to secure the helmet with openable, adjustable, fastening ends in a manner to apply minimal pressure to control bleeding and loosened and re-attached to prevent circulation stoppage and avoid aggravating intracranial pressure, wherein the segments of the helmet defining the ear observation holes are slit and variably secured together with straps having a first end secured on a first side of the slit, and an openable and closable adjustment fastener affixed to a second end of the strap; the fastener structured to secure to a corresponding fastener positioned on a second side of the slit in a manner so that the opening of the observation holes may be varied in size as the strap fastener is varied in position.

2. A helmet trauma bandage according to claim 1, wherein there are four exterior pouches positioned to cover respectively the forehead, back and sides of the head; each pouch structured with top openings leading into interiors into which hot or cold packs are inserted and secured therein with openable fasteners before removal.

3. A helmet trauma bandage according to claim 1, wherein the fasteners comprise corresponding hook and loop strips.

4. A helmet trauma bandage according to claim 1, wherein the helmet is constructed of a stretchable weather resistant material.

5. A helmet trauma bandage according to claim 1, wherein the helmet is color coded and configured to be placed on the patient to indicate the severity of a patient's injuries.

6. A method of using a head trauma bandage for covering a head wound of a patient comprising:
   a. affixing over a traumatized patient's head, a flexible stretchable helmet with
      i. periphery edges, segments, and an opening sized to fit about and cover a forehead, crown, ears, and back of a head of a patient with a head trauma; the helmet segments covering the ears defining ear opening observation holes to reveal any bleeding through the ears, and the helmet edges,
      ii. a sterile dressing liner affixed to the inside of the helmet; said helmet and liner with enough stretch when placed on the patient to apply minimal pressure to the head to control bleeding without aggravating intracranial pressure,
      iii. exterior pouches affixed to the exterior of the stretchable helmet structured to removably receive and secure therein hot or cold packs, and
      iv. a strap system releaseably affixed to the helmet periphery edges and structured to pass under a patient's chin to secure the helmet with openable, adjustable, fastening ends about the head in a manner to apply minimal pressure to control bleeding and loosened and re-attached to prevent circulation stoppage and avoid aggravating intracranial pressure wherein the segments of the helmet defining the ear observation holes are slit and variably secured together with straps having a first end secured on a first side of the slit, and an openable and closable adjustment fastener affixed to a second end of the strap; the fastener structured to secure to a corresponding fastener positioned on a second side of the slit in a manner so that the opening of the observation holes may be varied in size as the strap fastener is varied in position, and
   b. securing the strap system to hold the helmet bandage against the patient's head to apply minimal pressure to stop bleeding.

7. A method of using a helmet trauma bandage according to claim 6, including immobilizing the patient having head or spinal injuries first before applying the head trauma cap bandage.

8. A method of using a helmet trauma cap bandage according to claim 6, wherein the helmet trauma bandage is marked with different triage color codes to indicate the severity of a patient's injuries, and is selectively applied to a patient to indicate the type of medical response required.

9. A method of using a helmet trauma bandage according to claim 6, wherein the exterior pouches accommodate removable ice packs, which are selectively employed when needed to reduce swelling.

* * * * *